(12) United States Patent
Bäckström et al.

(10) Patent No.: US 8,119,619 B2
(45) Date of Patent: *Feb. 21, 2012

(54) PREGNANE STEROIDS AND THEIR USE IN THE TREATMENT OF CNS DISORDERS

(75) Inventors: Torbjörn Bäckström, Umeå (SE); Per Lundgren, Umea (SE); Ming-De Wang, Umea (SE); Inga-Maj Johansson, Vännäs (SE)

(73) Assignee: Umecrine AB, Umea (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/986,937

(22) Filed: Jan. 7, 2011

(65) Prior Publication Data

US 2011/0098259 A1    Apr. 28, 2011

Related U.S. Application Data

(63) Continuation of application No. 10/499,214, filed as application No. PCT/SE02/02423 on Dec. 20, 2002.

(30) Foreign Application Priority Data

Dec. 27, 2001  (SE) ....................................... 0104423

(51) Int. Cl.
*A01N 45/00* (2006.01)
(52) U.S. Cl. ........ 514/169; 514/176; 514/177; 514/178; 514/179; 514/180; 514/181; 514/182; 540/106; 540/107; 540/108; 540/109; 540/110; 540/111; 540/112; 540/114; 540/116; 540/36; 552/600
(58) Field of Classification Search .......... 514/169–172, 514/176–182; 540/94–99, 106–112, 114, 540/116; 552/600
See application file for complete search history.

(56) References Cited

U.S. PATENT DOCUMENTS

| 5,439,900 A | 8/1995 | Bukusoglu et al. |
| 2002/0072509 A1 | 6/2002 | Stein et al. |

FOREIGN PATENT DOCUMENTS

| WO | 96/15782 A1 | 5/1996 |
| WO | 98/50042 A1 | 11/1998 |
| WO | 98/50410 A1 | 11/1998 |
| WO | 98/50411 A1 | 11/1998 |
| WO | 99/45931 A1 | 9/1999 |
| WO | 00/21977 A1 | 4/2000 |

OTHER PUBLICATIONS

Office Action received for European Parent Application No. 02793723.4, mailed on Apr. 7, 2006, 4 pages.
Non Final Office Action received for U.S. Appl. No. 10/499,214, mailed on Mar. 2, 2010, 10 pages.
Notice of Allowance received for U.S. Appl. No. 10/499,214, mailed on Oct. 7, 2010, 9 pages.
Office Action received for Japanese Patent Application No. 2003-559519, mailed on Mar. 2, 2010, 8 pages ( 5 pages of English Translation & 3 pages of Office Action).
Akhondzadeh et al., "Potentiation of Muscimol-Induced Long-Term Depression by Benzodiazepines and Prevention or Reversal by Pregnenolone Sulfate", Pharmacological Research, vol. 38, No. 6, 1998, pp. 441-447.
Chen et al., "The Hyperphagic Effect of 3 alpha-Hydroxylated Pregnane Steroids in Male Rats", Pharmacology Biochemistry and Behavior, vol. 53, No. 4, 1996, pp. 777-782.
Clark et al., "Substrate Specificity of Cholesterol Oxidase", Clinical Chemistry, vol. 26, No. 5, 1980, p. 678.
Dorwald, F. Z., "Side Reactions in Organic Synthesis: A Guide to Succesul Synthesis Design", Wiley-VCH Verlag GmbH & Co. KGaA, 2005, 3 pages.
Hamilton, Niall M., "Therapeutic Potential of Steroids for CNS Disorders", Expert Opinion on Therapeutic Patents, vol. 11, No. 10, 2001, pp. 1523-1531.
Kokate et al., "Anticonvulsant Activity of Neurosteroids:Correlation with Gamma-Aminobutyric Acid-Evoked Chloride Current Potentiation", The Journal of Pharmacology and Experimental Therapeutics, vol. 270, No. 3, 1994, pp. 1223-1229.
Lance et al., "Indentaton of a Series of C21O2 Pregnanes from Fecal Extracts of a Pregnant Black Rhinoceros", Steroids, vol. 66, 2001, pp. 875-881.
Nagata et al., "Stereospecific Total Synthesis of RAC. 5α-pregnan-3β-ol-20-ONE", Tetrahedron Letters, No. 14, 1963, pp. 865-868.
International Search Report received for PCT Patent Application No. PCT/SE02/02423, mailed on May 6, 2003, 6 pages.
Prince et al., "5β-Pregnan-3β-ol-20-one, a Specific Antagonist at the Neurosteroid Site of the GABAA Receptor-Complex", Neuroscience Letters, vol. 135, 1992, pp. 273-275.
Prince et al., "Differential Antagonism by Epipregnanolone of Alphaxalone and Pregnanolone Potentiaion of [3H] Flunitrazepam Binding Suggests More than One Class of Binding Site for Steroids at GABAA Receptors", Neuropharmacology, vol. 32, No. 1, 1993, pp. 59-63.
Reddy et al. "Sigma (sigma1) Receptor Mediated Anti-depressant-like Effects of Neurosteroids in the Porsolt Forced Swim Test", NeuroReport, vol. 9, 1998, pp. 3069-3073.

*Primary Examiner* — Frederick Krass
*Assistant Examiner* — Nannette Holloman
(74) *Attorney, Agent, or Firm* — Morrison & Foerster LLP

(57) ABSTRACT

Steroid compounds possessing a hydrogen donor in 3beta position, either in the form of a hydroxy- or a sulfate group, function as efficient blockers of the 3alpha-hydroxy-pregnan-steroid action and thus have utility as therapeutic substances for the prevention and/or treatment of steroid related CNS disorders. Treatment methods based on the administration of these substances are disclosed, and these substances either alone or in combination are also suggested for the manufacture of pharmaceuticals for the treatment of many specific steroid induced CNS disorders.

17 Claims, 3 Drawing Sheets

PREGNANE STEROIDS AND THEIR USE IN THE TREATMENT OF CNS DISORDERS

CROSS-REFERENCE TO RELATED APPLICATION

Figure 1:
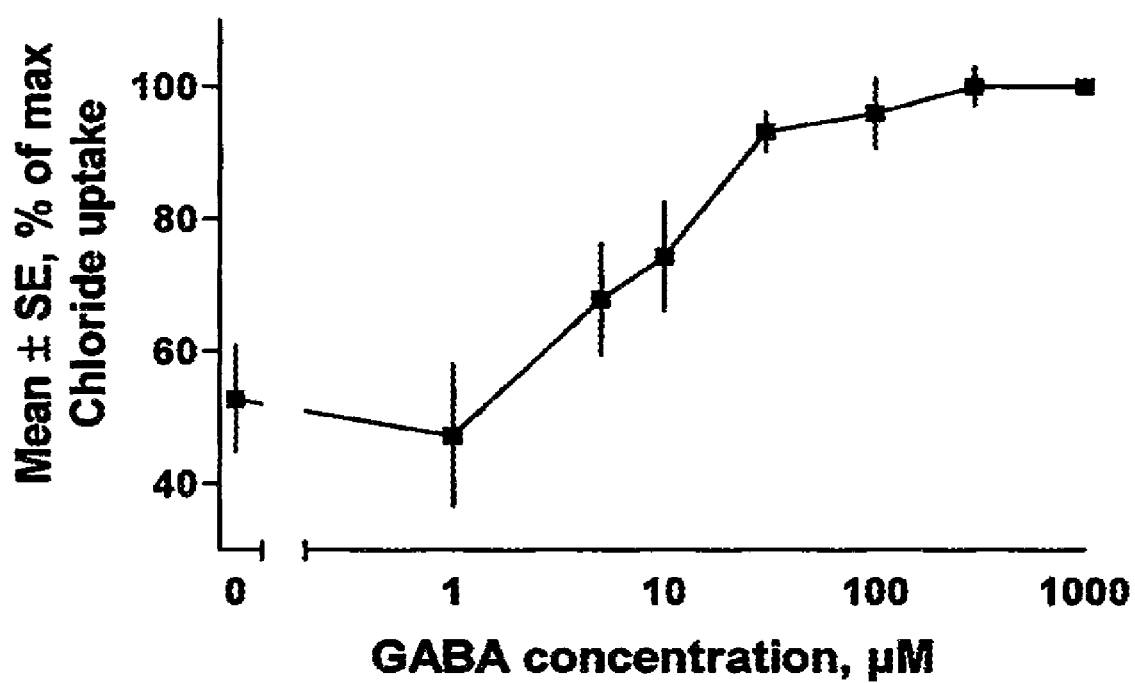

This application is a Continuation of U.S. patent application Ser. No. 10/499,214, filed Apr. 28, 2005, which is U.S. National Phase patent application of PCT/SE02/02423, filed Dec. 20, 2002, which claims priority to Swedish patent application Serial No. 0104423-9 filed Dec. 27, 2001, all of which are hereby incorporated by reference in their entirety.

BACKGROUND

The present invention concerns the treatment, alleviation or prevention of steroid related and/or steroid induced disorders of the central nervous system (CNS) and in particular specific steroid compounds for this purpose, their use for the manufacture of pharmaceuticals for said treatment, as well as methods of treatment.

The metabolites of pregnenolone, progesterone; desoxycorticosterone, cortisone and cortisol, known as pregnanolones as well as the metabolites of testosterone, androstendione and dehydroepiandrosterone, have all been the subject of various studies, at least partially elucidating their role in the neurological signal system in mammals.

The steroids inducing CNS symptoms and disorders of interest in the present application all share a common feature in comprising a 3alpha-hydroxy group, a 5alpha or 5beta pregnane steroid body, and a ketone or hydroxy group on position 17 or 20.

The steroids comprising the components 3alpha-hydroxy-5alpha/beta-pregnan-20-one/ol or 3alpha-hydroxy-5alpha/beta-androstan-17-one/ol have been shown to be important specific enhancers of the gamma-aminobutyric acid (A) receptor (GABA-A). They bind to the GABA-A receptor and act by enhancing the effect of GABA on the opening frequency of the GABA-A receptor and its opening duration. The effect is similar to the effects of both benzodiazepines and barbiturates. Said steroid compounds however have a binding site separate from that of both these compounds. Examples of such steroids and their number according to the Chemical Abstracts Registry/Chicago Academy of Science (CAS) are given in Table 1.

The steroid nomenclature is not entirely consistent, and therefore the nomenclature developed by the International Union of Pure and Applied Chemistry (IUPAC) will be used throughout this application.

TABLE 1

Nomenclature of the pregnanolone group

| IUPAC - nomenclature | CAS Number |
|---|---|
| 3alpha-hydroxy-5alpha-pregnan-20-one | 516-54-1 |
| 3alpha-hydroxy-5beta-pregnan-20-one | 128-20-1 |
| 3alpha,21-dihydroxy-5alpha-pregnan-20-one | 567-02-2 |
| 3alpha,21-dihydroxy-5beta-pregnan-20-one | 567-03-3 |
| 3alpha,11beta,17alpha,21-tetrahydroxy-5beta-pregnan-20-one | 53-02-1 |
| 3alpha-11beta,17alpha,21-tetrahydroxy-5alpha-pregnan-20-one | 302-91-0 |
| 3alpha-17alpha,21-trihydroxy-5alpha-pregnan-11,20-dione | 547-77-3 |
| 3alpha-17alpha,21-trihydroxy-5beta-pregnan-11,20-dione | 53-05-4 |

TABLE 1-continued

Nomenclature of the pregnanolone group

| IUPAC - nomenclature | CAS Number |
|---|---|
| 3alpha-hydroxy-5alpha-androstan-17beta-ol | 1852-53-5 |
| 3alpha-hydroxy-5beta-androstan-17beta-ol | — * |
| 3alpha-hydroxy-5alpha-androstan-17-one | 53-41-8 |
| 3alpha-hydroxy-5beta-androstan-17-one | 53-42-9 |

* CAS Number not found

Some of these steroids have been shown to have an ability to induce anesthesia at a high pharmacological dose. They can also be used as anti-epileptic agents, or as soporific agents. Some of these compounds have also been shown to possess anxiolytic effects in animal experiments. To reach these effects, however, high concentrations or high doses are required. Additionally, they appear as acute effects.

With respect to their direct CNS effects, these compounds are similar to benzodiazepins and barbiturates. However, they also have similar adverse effects as normally associated with benzodiazepins and barbiturates. The adverse effects of the endogenous 3alpha-hydroxy-pregnan-20-one-steroids or 3alpha-hydroxy-androstan-steroids are the basis for the negative CNS effects induced by these steroids. As the 3alpha-hydroxy-pregnane-steroids and 3alpha-hydroxy-androstan-steroids are endogenously produced and are metabolites of steroid hormones some of them essential for life, their production cannot easily be interrupted. These steroids are produced in high amounts during several days to weeks during the luteal phase of the menstrual cycle, that is after the release of an ovum from a mature ovarian follicle, during pregnancy and during stress. They are also produced within the brain.

Diseases Caused by 3alpha-hydroxy-steroids

Disorders that are caused by the action of endogenously produced 3alpha-hydroxy-5alpha steroids or 3alpha-hydroxy-5beta steroids on the GABA-A receptor are well characterized and understood. It is also known that 3alpha-hydroxy-5alpha/beta-steroids can induce tolerance to themselves and to other similar substances after exposure, and that abstinence effects occur at withdrawal of the 3alpha-hydroxy-5alpha/beta-steroids. In summary, it is now known that 3alpha-hydroxy-5alpha/beta-steroids cause CNS disorders through the above described three possible mechanisms: a) direct action, b) tolerance induction, and c) withdrawal effect. These mechanisms will be discussed in closer detail below.

a) Direct Action

It is established that 3alpha-hydroxy-5alpha/beta-steroids can directly cause inhibition of CNS functions. Examples of symptoms caused by the direct action of 3alpha-hydroxy-5alpha/beta-steroids are sedation, tiredness, memory disturbance, learning disturbance, disturbance of motor function, clumsiness, increased appetite and food cravings, negative mood as tension, irritability and depression which are the cardinal symptoms in the premenstrual syndrome and the worsening of Petit Mal epilepsy. Examples of this direct action can be divided into sedative and anesthetic effects; disturbance of motor function; effects on cognitive function, memory and learning; worsening of Petit Mal epilepsy; premenstrual symptoms; mood changes; induction of anxiety in test animals; hyperphagia and increased appetite; food cravings etc.

b) Tolerance

Continuous and long exposure to 3alpha-hydroxy-5alpha/beta-steroids causes a malfunctioning of the GABA-A receptor system. A tolerance develops and this tolerance is the initial step in a process that ultimately leads to stress sensitivity, concentration difficulties, and loss of impulse control and depression. The action of 3alpha-hydroxy-5alpha/beta-steroids have also been found to be a factor which reinforces drug dependency. This has been the focus of extensive research. The following themes have hitherto been the main subject of research: down regulation and decreased GABA function after long-term secretion of high amounts of 3alpha-hydroxy-5alpha/beta steroids; reduced benzodiazepine and 3alpha-hydroxy-5beta steroid sensitivity in PMS; and dependence induction.

c) Abstinence

A continuous but shorter exposure to 3alpha-hydroxy-5alpha/beta-steroids results in a withdrawal effect when the exposure is ended. This phenomenon occurs i.a. during menstruation when the production of 3alpha-hydroxy-5alpha/beta-steroids by the corpus luteum of the ovary is interrupted. This withdrawal phenomenon also occurs after-giving birth (post partum) when the 3alpha-hydroxy-5alpha/beta-steroid production by the placenta is interrupted. The same phenomenon is also noted when a period of stress is ended. As a response to stress, the adrenals have produced 3alpha-hydroxy-5alpha/beta-steroids. When this production is interrupted, withdrawal symptoms may occur.

Examples of conditions that are influenced by this withdrawal/abstinence phenomenon are partial epilepsy where the patient has an epileptic focus in the cerebral cortex where a worsening occurs at the withdrawal period during menstruation. This phenomenon is called "catamenial epilepsy". Other examples are menstrual related migraine and stress related migraine and mood changes postpartum. Abstinence is a sign of an earlier developed tolerance.

Similar symptoms and conditions are induced during treatment with steroid hormones as oral contraceptives, post-menopausal hormone replacement therapy, steroid treatment for inflammatory diseases and during intake of anabolic/androgenic steroids. The mechanisms being similar with direct effects, tolerance development and abstinence.

PRIOR ART

Prince and Simmons (*Neuropharmacology*, vol. 32, no. 1, pp. 59-63, 1993) have used a model relying on membrane fractions of whole male rat brain. In this sub-fraction of whole brain homogenate, the authors used the binding of a benzodiazepine, 3H-flunitrazepam, as a model for steroid effect and change of GABA-A receptor conformation. This test has been suggested as an indicator of allosteric modulation of the GABA-A receptor. The relationship between the change in flunitrazepam (FNZ) binding and change in chloride flow at GABA-stimulation is however uncertain and a change in binding can not be taken as a proof of change in chloride flow through the GABA-receptor or change in GABA-A receptor function. The change in chloride flow is the important effect.

The central question, i.e. if there exists a relationship between change in FNZ-binding and neuronal excitability, is even less clear and such conclusions cannot be drawn from results on FNZ-binding. A change in FNZ-binding properties or absence of such change in binding properties does not imply a change or absence of change in neural activity or GABA-A mediated chloride flow.

It is also well known that the GABA-A receptor contains several sub-units that can be combined in multiple ways. It is known that certain combinations lack steroid recognition site. It is also known that the effect of steroid on the binding of a convulsant substance TBPS (t-butylbicyclo-phosphorothionate) differs in different brain regions. Further, it is known that the binding of TBPS varies with the oestrus cycle in female rats indicating an effect change related to the ovarian hormone production. These changes related to oestrus cycle can of course not be noticed in male rats, as used in the studies of Prince and Simmons (supra).

U.S. Pat. No. 5,232,917 (Bolger et al.) and U.S. Pat. No. 5,939,545 (Upasani et al.) disclose a number of 3alpha-hydroxy steroids. Both these patents concern the agonistic modulation of the GABA-A receptor. In other words, the patents are focussed on the benzodiazepine like effect of the 3alpha-hydroxy-5alpha/beta-steroids. All steroids that are modulators of the GABA-A receptor have the common feature of one 3alpha-hydroxy structure. The 3beta-hydroxy steroids mentioned in these documents were only used as controls to show that the 3alpha-hydroxy-steroids were specific. Steroids with only a 3beta-hydroxy structure have never been shown to possess a GABA-A receptor modulating effect. In all cases where an effective GABA-A receptor-modulating effect is noticed, the steroid has a 3alpha-hydroxy group.

WO 99/45931 (Bäckström & Wang) discloses the antagonistic effect of one particular steroid, namely 3beta-hydroxy-5alpha-pregnan-20-one but is silent about the other 3beta-hydroxy-steroids and the 3beta-sulfate pregnan steroids now described in this application.

The antagonistic effect of 3beta-OH-5alpha-pregnan-20-one against 3alpha-OH-5alpha/beta-pregnan-20-one was first disclosed by Wang et al. (Wang M D., Bäckström T. and Landgren S. (2000) *The inhibitory effects of allopregnanolone and pregnanolone on the population spike, evoked in the rat hippocampal CA1 stratum pyramidale in vitro, can be blocked selectively by epiallopregnanolone.* Acta Physiol Scand 169, 333-341). In that paper, a dose dependent antagonistic effect of 3beta-OH-5alpha-pregnan-20-one on two of the 3alpha-OH-5alpha/beta-steroids is described.

It remains a challenge to find specific blockers of the 3alpha-hydroxy-pregnan-steroid action, which compounds are physiologically safe and suitable, and which additionally are applicable in physiologically acceptable doses.

One objective of the present invention is thus to identify such specific blockers and to make available novel pharmaceuticals and methods for the treatment, alleviation or prevention of steroid related and/or steroid induced CNS disorders.

Further objectives, the associated solutions and their advantages will be obvious to a killed person upon familiarizing himself with the description, examples and claims

SUMMARY OF THE INVENTION

The present inventors have found that steroid compounds possessing a hydrogen donor in 3beta position, either in the form of a hydroxy- or a sulphate group, surprisingly function as efficient blockers of the 3alpha-hydroxy-pregnan-steroid action and thus have utility as therapeutic substances for the prevention and/or treatment of steroid related or steroid induced CNS disorders.

The present inventors present seven (7) compounds as substances for use for the prevention and/or treatment of steroid related or steroid induced CNS disorders, and for the manufacture of pharmaceuticals for this purpose, namely 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate (Table 2).

One aspect of the present invention is the therapeutic use of the above compounds as blocking substances against the 3alpha-hydroxy-pregnan-steroid action. In addition, these substances are now suggested for the manufacture of pharmaceuticals for the treatment of many specific steroid related or steroid induced CNS disorders and for use in methods of treatment, according to the attached claims, which are incorporated herein by reference.

SHORT DESCRIPTION OF THE DRAWINGS

The intention will be described in closer detail in the following description and examples, with reference to the tables incorporated into the description, and the attached drawings, in which FIG. 1 shows the mean (SEM) percentage change in chloride uptake with increasing dosage of GABA. These results show that the chloride uptake is GABA dependent and that the method used works.

Figure 2:
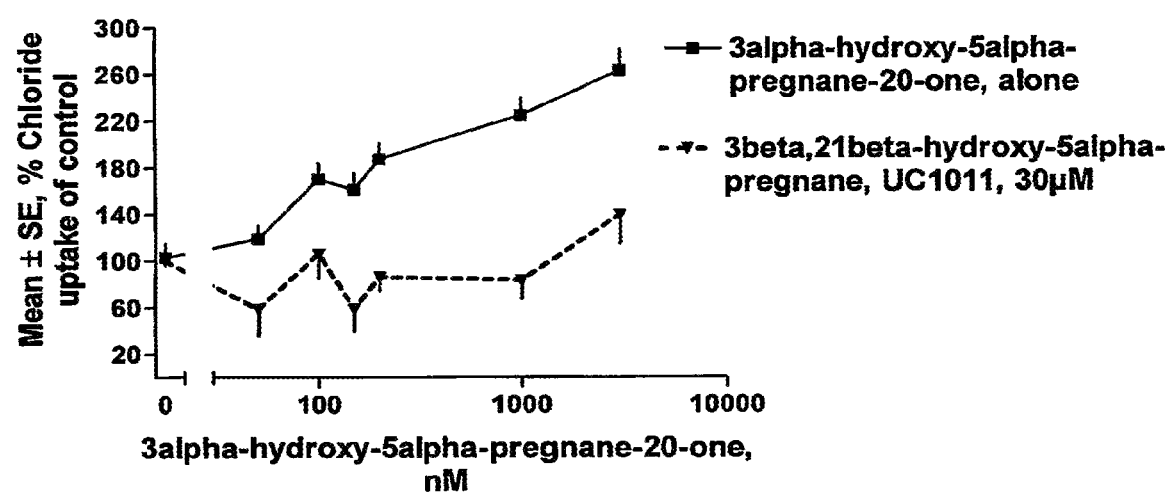

FIG. 2 shows the mean (SEM) percentage change in chloride uptake with increasing dosage of 3alpha-hydroxy-5alpha-pregnan-20-one alone (nM, X-axis) in the presence of 10 µM of GABA. The second line shows the mean (SEM) percentage change in chloride uptake with increasing dosage of 3alpha-hydroxy-5alpha-pregnan-20-one (nM, X-axis) in the presence of 10 µM of GABA, and 30 µM of 3beta,20beta-dihydroxy-5alpha-pregnane, UC1011, (CAS No. 516-53-0). The Figure show that the increase in chloride uptake induced by 3alpha-hydroxy-5alpha-pregnan-20-one is blocked by 30 µM of 3beta,20beta-dihydroxy-5alpha-pregnane, UC1011, (CAS No. 516-53-0), ($p<0.001$).

Figure 3:
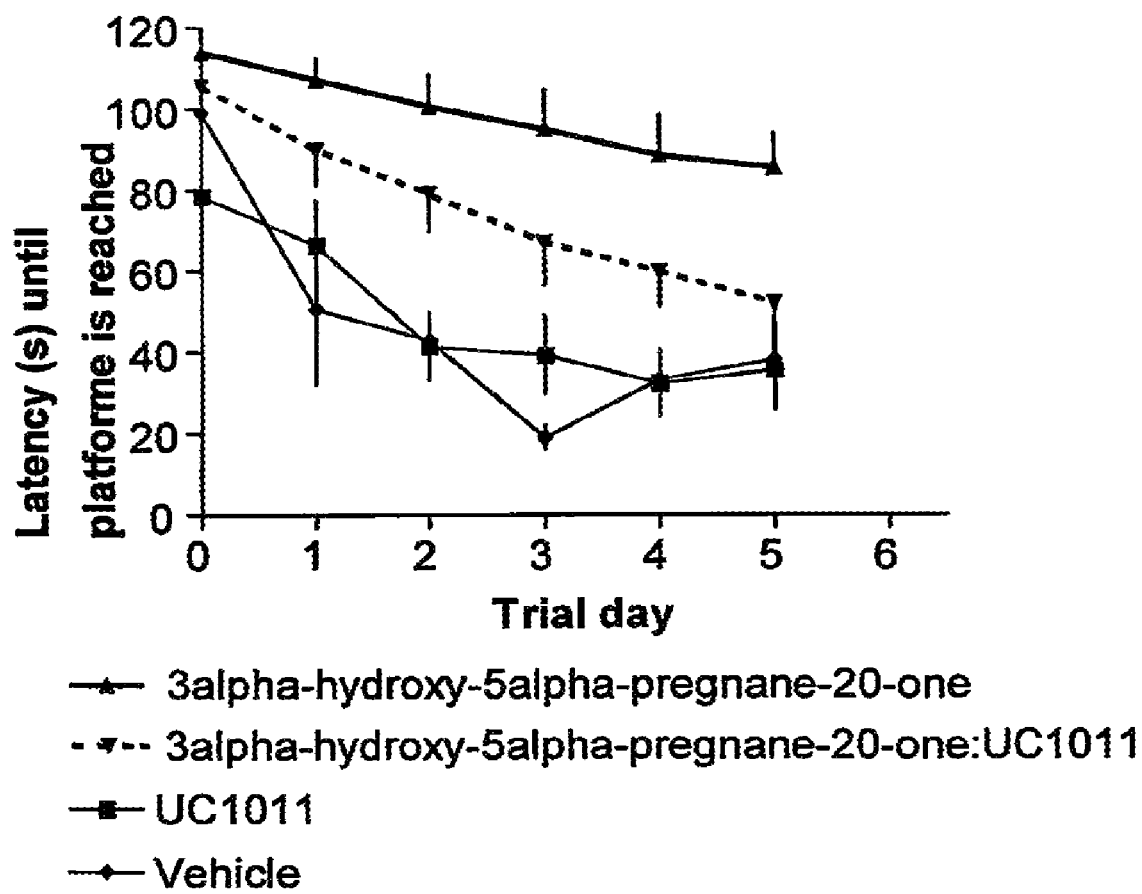

FIG. 3 shows the mean (SEM) latency (Y-axis, seconds) until a group of rats could find a hidden platform in the Morris Water Maze during a series of trials over six days (X-axis, days). Each rat does four trials per day. The control rats and the rats that received only 3beta,20beta-dihydroxy-5alpha-pregnane, UC1011 learn to find the platform on the tired day of training and swims directly to the platform when released into the water. The rats that receive 3alpha-hydroxy-5alpha-preganane-20-one do not learn significantly within six days. When the 3alpha-hydroxy-5alpha-preganane-20-one effect is blocked with 3beta,20beta-dihydroxy-5alpha-pregnane, UC1011 they start to learn significantly on the $4^{th}$ day of training

DESCRIPTION OF THE INVENTION

Before the present invention is described, it is to be understood that the terminology employed herein is used for the purpose of describing particular embodiments only and is not intended to be limiting, since the scope of the present invention will be limited only by the appended claims and equivalents thereof.

In particular, it must be noted that, as used in this specification and the appended claims, the singular forms "a", "an", and "the" also include plural referents unless the context clearly dictates otherwise.

In the following description, the terms "steroid related" and "steroid induced" as in "steroid related disorders" are meant to encompass the three possible mechanisms by which steroids act on the central nervous system: a) direct action, b) tolerance induction, and c) withdrawal effect. Examples of such disorders have been given above, but they are meant to illustrate each mechanism, and not to be construed as limiting the invention.

The term "blocking" is meant to define an effect where in this case the 3alpha-hydroxy-5alpha/beta-steroids are prevented from acting on the GABA-R receptor. It is understood that "blocking" is an entirely different effect than meant by "modulation" or "repression" or similar terms, which suggest that an action is still taking place, but to a lesser extent or at a slower rate.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivate or a pro-drug, such as pharmaceutically acceptable salts, sulphates and esters. The manufacture of pharmaceutical compositions for different routes of administration falls within the capabilities of a person skilled in galenic chemistry.

The terms "administration" and "mode of administration" as well as "route of administration" are also used in their widest sense. The pharmaceutical composition of the present invention may be administered in a number of ways depending largely on whether a local, topical or systemic mode of administration is most appropriate for the condition be treated. These different modes of administration are for example topical (e.g., on the skin), local (including ophthalmic and to various mucous membranes such for example vaginal and rectal delivery), oral or parenteral and pulmonary, including the upper and lower airways.

The preparation of such compositions and formulations is generally known to those skilled in the pharmaceutical and formulation arts and may be applied to the formulation of the composition of the present invention.

With the term "antagonist" is meant a substance that hinders another substance, an agonist, to induce its effect. In this application the terms antagonist and blocker are used simultaneously.

The present inventors have surprisingly shown that pharmaceutically suitable and practically applicable doses of steroids having a hydrogen donor in 3beta position can block the action of 3alpha-hydroxy-5alpha/beta-steroids in vitro, thus blocking the development of the negative effects of 3alpha-hydroxy-5alpha/beta-steroids. Both the mechanism of action of 3alpha-hydroxy-5alpha/beta-steroids in the development of CNS disorders and the mechanism of action of 3beta-hydroxy-5alpha/beta-pregnan or 3beta-sulfate-5alpha/delta5-pregnan/pregnen steroids in their interactions with 3alpha-hydroxy-5alpha/beta-steroids have been addressed. Examples of such compounds are given in Table 2.

TABLE 2

List of 3beta-hydroxy-5alpha/beta-pregnan or 3beta-sulfate-5alpha/delta5-pregnan/pregnen-steroids tested in the present invention

| Substance* | Product name | CAS Number |
| --- | --- | --- |
| 1) 3beta,20beta-dihydroxy-5alpha-pregnane | UC1011 | 516-53-0 |
| 2) 3beta,20alpha-dihydroxy-5beta-pregnane | UC1013 | 80-90-0 |
| 3) 3beta-hydroxy-delta5-pregnen-20-one-sulfate, sodium salt | UC1018 | 1852-38-6 |
| 4) 3beta-hydroxy-5beta-pregnan 20-one | UC1014 | 128-21-2 |
| 5) 3beta,21-dihydroxy-5beta-pregnan-20-one | UC1015 | Not found |
| 6) 3beta-hydroxy-5alpha-pregnan-20-one-sulfate, sodium salt | UC1016 | Not found |
| 7) 3beta hydroxy-5alpha-pregnan-11,20-dione | UC1017 | Not found |
| 8) 3beta-hydroxy-5alpha-pregnan-20-one | UC1010 | 516-55-2 |
| 9) 3beta-hydroxy-5alpha-pregnan-20-one-acetate, | UC1012 | 906-83-2 |

*The substances were obtained from Steraloids Inc., USA, and from Sigma Chemicals Co.

The present invention concerns all steroids having a hydrogen donor in 3beta position, in particular a hydroxy- or sulphate group, here exemplified by the 3beta-hydroxy-pregnan-steroids and the 3beta-sulfate-pregnan-steroids described in Table 2. The present inventors have shown that these steroids are antagonists and able to block the effect of 3alpha-hydroxy-5alpha/beta-pregnan-steroid effects in the central nervous system (CNS). Surprisingly, simultaneous treatment with a 3alpha-hydroxy-pregnan-steroids and 3beta-hydroxy-pregnan-steroids and 3beta-sulfate-pregnan-steroids mentioned in Table 2, inhibits the uptake and chloride flux thru the GABA-A receptor induced by the 3alpha-hydroxy-pregnan-steroid.

One advantage of the invention is that 3beta-hydroxy- and 3beta-sulfate-pregnan/pregnen-steroids, and in particular 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate efficiently block and antagonize the GABA-A receptor modulation effect of 3alpha-hydroxy-5alpha/beta-pregnan-steroids. A particular advantage is that this blocking is achieved at pharmacologically and physiologically suitable concentrations.

3beta-hydroxy-5alpha/beta-pregnan-steroids and 3beta-sulfate-5alpha/beta-pregnan/pregnen-steroids, and in particular 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate, sodium salt have been shown by the present inventors to inhibit the effect of 3alpha-hydroxy-5alpha/beta-pregnan-steroids in a GABA-A receptor model of chloride uptake. The GABA-A receptor is a chloride channel and the GABA-A receptor exercises its action via changing the influx of chloride through the channel. It is well known in the art that the neuronal activity in the brain is decreased when the GABA-A receptor is open and a large amount of chloride flux into the cell. It is also well known that there is a relation between the amount of chloride moving in and the clinical effect of a GABA-A receptor active drug.

Benzodiazepines and barbiturates exercise their action via this mechanism. This, however, also accounts for the adverse effects of these drugs. The new and surprising finding behind the present invention is that it is possible to block the action of 3alpha-hydroxy-5alpha/beta-pregnan-steroids on the chloride uptake by administering 3beta-hydroxy and 3beta-sulfate-pregnan/pregnen-steroids in pharmaceutically and physiologically acceptable amounts. The GABA-A receptors used in the experiments were collected from rat cortical tissue, which is a representative part of the brain for measurement of GABA-A receptor effects. It can be assumed, with a high degree of confidence, that the results achieved in this model can be confirmed in higher mammals and in human patients.

As has been discussed above, there are a number of symptoms and conditions that are related to 3alpha-hydroxy-5alpha/beta-pregnan-steroids, and where blocking the 3alpha-hydroxy-5alpha/beta-pregnan-steroid effect would be a treatment of the condition in question. The present inventors now make available substances and methods for such blocking.

In the experimental work reported by Prince and Simmons (supra) an indirect ligand-binding assay was used. By studying the FNZ-binding alone, one can however not assume that the same effect will be seen in a neural activity in vivo. This has also not been claimed by Prince and Simmons in their paper. They have only discussed implications for binding sites of steroids and if these sites are the same or not. This is not a new discussion and the possibility of several binding sites for steroids has been indicated in earlier publications. The only conclusion drawn by them and the possible conclusions to be drawn using their experimental design and model is that the steroid changes the binding of FNZ differently and has some interactions on the FNZ-binding. No conclusion of effects on neural activity or on clinical implications can be drawn from the results of Prince and Simmons.

The present inventors have surprisingly shown that pharmaceutically suitable and useable doses of 3beta-hydroxy-5alpha/beta-pregnan- and 3beta-sulfate-pregnan/pregnen-steroids, and in particular 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate can block the action of 3alpha-hydroxy-5alpha/beta-steroids, thus blocking the development of the negative effects of 3alpha-hydroxy-5alpha/beta-steroids. The inventors have determined both the mechanism of action behind &orders caused by 3alpha-hydroxy-5alpha/beta-steroids, and the mechanism of action behind the interaction of 3beta-hydroxy-5alpha/beta-pregnan or 3beta-sulfate-5alpha/delta5-pregnan/pregnen-steroids with 3alpha-hydroxy-5alpha/beta-steroids. It is well-established in the art that 3alpha-hydroxy-5alpha/beta-steroids cause CNS disorders through three possible mechanisms a) direct action, b) tolerance induction, and c) withdrawal effect.

The present invention also concerns the mechanism underlying the effect of steroids possessing a hydrogen donor in 3beta position, in particular 3beta-hydroxy-5alpha/beta-pregnan-20-one-steroids and 3beta sulfate-5alpha/beta pregnane or pregnene steroids, exemplified by 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. The present invention makes it possible to identify and to synthesize compounds sharing these features, or functional analogues, mimicking the function of these substances.

One embodiment of the present invention is a process for the screening, isolation or synthesis of drug-candidates being substances capable of blocking the action of 3alpha-hydroxy-5alpha/beta-steroids, thus blocking the development of the negative effects of 3alpha-hydroxy-5alpha/beta-steroids, comprising a step where a structural or functional similarity with the above exemplified compounds is used as a selection criteria in screening or isolation, or as a criteria for validating the end-product in synthesis. Another embodiment of the invention encompasses compounds identified or synthesized using this process step.

These substances have utility as therapeutics and as components for the manufacture of therapeutic substances. Substances comprising the feature of 3beta-hydroxy-5alpha/beta-pregnan-20-one are effective as blockers or antagonists against effects caused by 3alpha-5alpha/beta-steroids, in particular GABA-A receptor modulating effects.

Compared to previously disclosed inventions, e.g. Bolger et al., U.S. Pat. No. 5,232,917 and Upasani et al., U.S. Pat. No. 5,939,545, an important fact is that 3beta-hydroxy-5alpha-pregnan-20-one-steroids have never, to the best knowledge of the inventors, been shown to be modulators of the GABA-A receptor, neither as positive (enhancing) modulators or negative (inhibitory) modulators. In addition, the use of 3beta-hydroxy-5alpha/beta-pregnan-steroids or 3beta-sulfat-5alpha/delta5-pregnan/pregnen-steroids as antagonists or blockers of the GABA-A receptor modulating 3alpha-hydroxy-5alpha/beta-steroids does not seem to have been tested. Importantly, the present invention is not proposing that 3beta-hydroxy-5alpha/beta-pregnan-20-one-steroids or 3beta-sulfat-5alpha/beta-pregnan-20-one steroids would be modulators of the GABA-A receptor. An important feature of the present invention is that 3beta-hydroxy-5alpha/beta-pregnan or 3beta-sulfate-5alpha/delta5-pregnan/pregnen-steroids have utility as antagonists, or blockers, and that they prevent the effects by 3alpha-hydroxy-5alpha/beta-pregnan-steroids.

Bolger et al., U.S. Pat. No. 5,232,917 and Upasani et al., U.S. Pat. No. 5,939,545 do not disclose any 3beta-hydroxy-5alpha/beta-pregnan-steroid as being a modulator of the GABA-A receptor, neither in the patents or in their corresponding scientific publication (Lan N. C., Gee K. W., Bolger M. B. & Chen J. S. (1991), Differential responses of expressed recombinant human gamma-aminobutyric acidA receptors to neurosteroids. *Journal of Neurochemistry*, 57(5): 1818-1821.)

Consequently, as a general aspect of the invention, the inventors make available chemical compounds capable of blocking the action of 3alpha-hydroxy-pregnan-steroids on the human GABA-A receptor, wherein said compounds have a hydrogen donor in 3beta position in the form of a group chosen among hydroxy and sulphate groups. Preferably said compounds are chosen among 3beta,20beta-dihydroxy-5alpha-pregnane, 3beta,20alpha-dihydroxy-5beta-pregnane, 3beta,21-dihydroxy-5beta-pregnan-20-one, 3beta-hydroxy-5alpha-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate.

Another aspect of the invention is a pharmaceutical composition comprising a compound capable of blocking the action of 3alpha-hydroxy-pregnan-steroids on the human GABA-A receptor, wherein said compound has a hydrogen donor in 3beta position in the form of a group chosen among a hydroxy and a sulphate group, said compound being present in a pharmaceutically efficient amount, optionally in admixture with a pharmaceutically acceptable carrier. Preferably said compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11, 20-dione, 3beta-hydroxy-5alpha-pregnan-20-one-acetate and 3beta-hydroxy-5alpha-pregnan-20-one-sulfate. Preferably said compound is present in the form of a suitable and pharmaceutically acceptable salt, most preferably a sodium salt.

Another aspect of the present invention is a general method for the treatment and/or prevention of steroid related CNS disorders in human patients, wherein at least one compound capable of blocking the action of 3alpha-hydroxy-pregnan-steroids on the human GABA-A receptor is administered to said patient. Preferably said compound has a hydrogen donor in 3beta position in the form of a group chosen among a hydroxy and a sulphate group, and most preferably said compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Preferably said compound is used in the form of a suitable and pharmaceutically acceptable salt, most preferably a sodium salt.

According to the present invention, said at least one compound is administered through one of the following routes of administration: intravenously, nasally, per rectum, intravaginally, percutaneously and orally. According to one preferred embodiment, said at least one steroid is administered intravenously. According to another preferred embodiment, said at least one steroid is administered nasally.

Nasal administration in particular is a promising alternative, as it offers the benefits of ease and the possibility of self-administration by the patient. Self-administration has the advantage of allowing the patient to adjust the dose or the frequency of medication according, either according to a subjective evaluation of their condition, or according to a schedule prescribed by the treating physician. The term "schedule prescribed by the treating physician" includes the alternative where the patient makes a subjective evaluation of his/her condition, either unaided or aided by a questionnaire or a range or scale, or using an algorithm or a computer programme, indicating the suitable next dose.

Percutaneous administration, using the substances formulated as a cream, a gel, and an ointment or in the form of slow-release adhesive medicine patches, is another possible form of administration, similarly suitable for self-medication. The advantages of self-administration listed above apply also to percutaneous administration, with the added advantage that the administration can easily be interrupted if desired or necessary, e.g. by removing the medicine patch.

In any of these or other routes of administration, the formulation of the composition may be adapted or adjusted according to normal pharmacological procedures, comprising the effective pharmaceutical in a chemical form, suitable for the chosen route, together with suitable adjuvants and vehicles, conventionally used and well-known to a person skilled in the art.

Conventionally used adjuvants and vehicles for oral administration are for example fillers or suspending agents like titanium dioxide, lactose anhydride, silica, silica colloidalis, methylcellulose, magnesium stearate, microcrystalline cellulose and the like.

Conventionally used adjuvants and vehicles for intravenous administration are for example sterile water for injections (WFI), sterile buffers (for example buffering the solution to pH 7.4) and the like.

Conventionally used adjuvants and vehicles for transdermal administration are for example vaseline, liquid paraffin, glycerol, water and the like.

The dose will naturally vary depending on the mode of administration, the particular condition to be treated or the effect desired, the gender, age, weight and health of the patient, as well as possibly other factors, evaluated by the treating physician. According to the present invention, when said at least one steroid is administered intravenously, a suitable interval is that of about 0.2 to 200 mg per kg body weight. Preliminary studies in animals indicate that a preferred interval for intravenous administration is about 20 to 100 mg per kg body weight.

Corresponding dose intervals for other modes of administration may easily be calculated by a person skilled in the art, and—if necessary—verified through non-inventive animal tests or pre-clinical or clinical studies.

One embodiment of the present invention is a method for treatment of steroid related or steroid induced CNS disorders, in particular premenstrual syndrome, wherein tolerance development is prevented and the down-regulation of the GABA-A receptor prevented by administration of at least one substance according to the invention. This treatment would preserve the sensitivity of the GABA-A system and inhibit the development of a less sensitive state during the luteal phase. It has been shown in rat that there is a change of the GABA-A receptor during chronic progesterone treatment. The treatment with 3beta-hydroxy-5alpha/beta-pregnan-steroids or 3beta-sulfate-5alpha/delta5-pregnan/pregnen-steroids according to the present invention sets out to prevent the development of tolerance, and thus to hinder the withdrawal effect when the 3alpha-hydroxy-5alpha/beta-steroid is withdrawn.

A tolerance development will decrease the sensitivity for GABA-A enhancing substances endogenously produced like the 3alpha-hydroxy-5alpha-pregnan-20-one or benzodiazepines. When the drug is rapidly removed, like at the end of the luteal phase in the menstrual cycle a rebound effect arrives after the withdrawal of the 3alpha-hydroxy-5alpha-pregnan-steroids. Such a situation is found in humans with increase in migraine and epileptic seizures during the menstruation shortly after the end in production and withdrawal of the steroids.

Another embodiment of the present invention is accordingly a method for treatment or prevention of tolerance development and/or withdrawal symptoms, by administration of at least one substance according to the invention.

The present invention further concerns a method for the treatment and/or prevention of steroid related or steroid induced mood disorders in human patients described above, according to which method at least one 3beta-hydroxy-5alpha/beta-pregnan-steroid or a 3beta-sulfate-5alpha/delta5-pregnan/pregnen-steroid is administered to said patient. Preferably said steroid compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

Suitable routes of administration are for example the following: intravenously, nasally, per rectum, intra vaginally, percutaneously and orally.

For the treatment of many CNS disorders and for the uses as an anti-anaesthetic, it is however preferred that, the effective compound or compounds is/are administered intravenously.

Suitable doses according to the invention, in intravenous administration, are doses in the interval of about 0.2 to about 200 mg per kg body weight, preferably about 20 to about 100 mg/kg.

As described above, the formulation of the composition may be adapted or adjusted according to normal pharmacological procedures. Further, the dose will naturally vary depending on the mode of administration, the particular condition to be treated or the effect desired, the gender, age, weight and health of the patient, as well as possibly other factors, evaluated by the treating physician.

Further, the present invention encompasses methods for the treatment and/or prevention of steroid related or steroid induced CNS disorders in human patients, according to which method one or more 3beta-hydroxy-5alpha/beta-pregnan-steroids (see Table 2) is/are administered in a pharmaceutically and physiologically acceptable dose to said patient. Preferably said steroid compound is chosen among 3beta, 20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

Examples of symptoms and conditions caused by the direction action of 3alpha-hydroxy-5alpha/beta-steroids are sedation, tiredness, memory disturbance, learning disturbance, disturbance of motor function, clumsiness, increased appetite and food cravings, negative mood as tension, irritability and depression which are the cardinal symptoms in the premenstrual syndrome and the worsening of Petit Mal epilepsy.

Conditions and symptoms caused by tolerance development after long time (days) exposure to 3alpha-hydroxy-5alpha/beta-steroids are e.g. stress sensitivity, concentration difficulties, stress or menstrual cycle linked difficulties in concentration, sleep disorders, tiredness, loss of impulse control and depression. 3alpha-hydroxy-5alpha/beta-steroids also reinforce drug dependency. According to the present invention, these conditions or symptoms can be prevented, alleviated or treated by the administration of at least one 3beta-hydroxy-5alpha/beta-pregnan-steroid or a 3beta-sulfate-5alpha/delta5-pregnan/pregnen-steroid to the patient. Preferably said steroid compound is chosen among 3beta20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

A continuous but shorter exposure to 3alpha-hydroxy-5alpha/beta-steroids gives a withdrawal effect when the exposure is ended. This phenomenon occurs during menstruation when the production of 3alpha-hydroxy-5alpha/beta-steroids by the corpus luteum of the ovary is interrupted. This withdrawal phenomenon also occurs after giving birth (post partum) when the 3alpha-hydroxy-5alpha/beta-steroid production by the placenta is interrupted. The same phenomenon is also noted when a period of stress is ended and the 3alpha-hydroxy-5alpha/beta-steroids produced by the adrenal during the stress are interrupted. Examples of conditions that are influenced by this withdrawal/abstinence phenomenon are partial epilepsy where the patient has an epileptic focus in the cerebral cortex where a worsening occurs at the withdrawal period during menstruation. This phenomenon is called "catamenial epilepsy". Other examples are menstrual related migraine and stress related migraine and mood changes post partum. Abstinence is a sign of an earlier developed tolerance.

Examples of such disorders, believed to be steroid related or steroid induced, include the following: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, menstrual cycle linked difficulties in concentration, menstrual cycle linked sleep disorders and tiredness. There are strong indications that also obesitas and increased apetite, as well as some forms of balance disturbanceses are steroid related or steroid induced. The present invention thus offers substances and methods for treatment, alleviation or prevention of these conditions.

One preferred embodiment of the invention, addressing a problem afflicting numerous women, is a method for the treatment and/or prevention of side effects of postmenopausal therapy in human patients, according to which method at least one 3beta-hydroxy-5alpha/beta-pregnan-steroid or a 3beta-sulfate-5alpha/delta5-pregnan/pregnen-steroid is administered to said patient. Preferably said steroid compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

Another preferred embodiment of the invention is the treatment and/or prevention of side effects of oral contraceptives in human patients, in which treatment at least one 3beta-hydroxy-5alpha/beta-pregnan-steroid or a 3beta-sulfate-5alpha/delta5-pregnan/pregnen-steroid is administered to said patient. Preferably said steroid compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

In this application, it is preferred, that the effective composition of at least one of the above exemplified 3beta-hydroxy-5alpha/beta-pregnan-steroids or a 3beta-sulfate-5alpha/delta5-pregnan/pregnen-steroids is/are administered together with the oral contraceptive, taken by the patient. Nasal and percutaneous administrations are also suitable routes of administration.

One particular embodiment of the present invention is thus a pharmaceutical composition comprising an oral contraceptive and a therapeutically suitable dose of at least one chemical compound capable of blocking the action of 3alpha-hydroxy-pregnan-steroids on the human GABA-A receptor, wherein said compound/-s has/have a hydrogen donor in 3beta position in the form of a group chosen among hydroxy and sulphate groups. Preferably said compound is chosen among 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate. Most preferably said compound is used in the form of a suitable and pharmaceutically acceptable salt, most preferably a sodium salt.

Further, within the scope of the above embodiment, the dose of the chemical compound capable of blocking the action of 3alpha-hydroxy-pregnan-steroids on the human GABA-A receptor is preferably adjusted to the levels of endogenous steroids during stress or the menstrual period. According to the invention, a chemical compound capable of blocking the action of 3alpha-hydroxy-pregnan-steroids on the human GABA-A receptor may included in an oral contraceptive both in order to alleviate or remove the side-effects of oral contraceptives, or in order to alleviate or remove any unwanted effect of the periodical changes in endogenous steroids.

In general, the present invention encompasses the use of 3beta-hydroxy-5alpha/beta-pregnan-steroid or a 3beta-sulfate-5alpha/delta5-pregnan/pregnen-steroid, and in particular 3beta,20beta-dihydroxy-5alpha-pregnane, 3beta,20alpha-dihydroxy-5beta-pregnane, 3beta-hydroxy-5beta-pregnan 20-one, 3beta,21-dihydroxy-5beta-pregnan-20-one, 3beta-hydroxy-5alpha-pregnan-11,20-dione, 3beta-hydroxy-5alpha-pregnan-20-one-acetate and 3beta-hydroxy-5alpha-pregnan-20-one-sulfate, either alone or in combination, for the manufacture of a pharmaceutical for the treatment or prevention of any one of the 3alpha-hydroxy-5alpha/beta-pregnan-steroid related or -induced disorders described in the specification, and especially one or several of the following disorders: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, menstrual cycle linked difficulties in concentration, menstrual cycle linked sleep disorders and tiredness. Preferably said compound is used in the form of a suitable and pharmaceutically acceptable salt, most preferably a sodium salt.

EXAMPLES

The present invention is based on experiments in vitro, performed to confirm the blocking effect of 3beta-hydroxy-5alpha/beta-pregnan or 3beta-sulfate-5alpha/delta5-pregnan/pregnen-steroids on 3alpha-hydroxy-5alpha/beta-pregnan-steroids. The results from the in vitro tests are to be confirmed in in vivo tests, presently scheduled by the inventors. One animal test however already indicates that the surprising blocking effect is encountered also in living test animals.
Cortical Tissue Homogenate Study In these studies cortical tissue from mature male rats was homogenized in buffer. As a result of this procedure a suspension of small vesicles was formed, said vesicles having GABA-A receptors on their surface. When radioactive chloride is added to this suspension, a certain amount will enter the vesicles. This amount is related to how much open the GABA-A receptor is. Drugs that open the receptor will increase the amount of chloride in the vesicles in relation to the dosage of the drug. Similarly, drugs that close the GABA-A receptor will decrease the amount of chloride moving into the vesicles. The labeled chloride outside of the vesicles was washed away and separated from the chloride inside. The amount of radioactively labeled chloride inside the vesicles was thereafter measured in a fluid scintillator and a curve drawn.

At each experiment, a control of increasing dosages of GABA was used to ensure that the tissue sample is working properly. The results of a number of such controls are shown in FIG. 1. A second control was used to enhance the effect of 10 μM of GABA by adding increasing dosages 3alpha-hydroxy-5alpha-pregnan-20-one. The results of several such controls are shown in FIG. 2. In FIG. 2, an example of one of the blocking steroids is shown. As can be noted the effect of 3alpha-hydroxy-5alpha-pregnan-20-one was blocked and the amount of chloride moving in was not different from the amount when 10 μM of GABA by itself was used.

Table 3 gives a summary of the 3beta-hydroxy-5alpha/beta-pregnan or 3beta-sulfate-5alpha/delta5-pregnan/pregnen-steroids showing a blocking effect. One of the steroids, 3beta-hydroxy-5alpha-pregnan-20-one, UC1010, has been previously disclosed in patent application WO 99/45931 and is included here only for the sake of completeness. An other steroid 3beta-hydroxy-delta5-Pregnen-20-one, sulfate, sodium salt (UC1018) has in addition effects on other CNS receptors besides the GABA-A receptor and is therefore not suitable as medication to humans and is also only included as the sake of completeness.

Table 3 shows the results on chloride uptake through the GABA-A receptors when testing only using the known GABA-A agonist 3alpha-hydroxy-5alpha-pregnan-20-one. Further it shows the blocking effect by the 3beta-hydroxy and 3beta sulfate-pregnan/pregnen-steroids on the change in chloride uptake induced by 3alpha-hydroxy-5alpha-pregnan-20-one. The effect is shown as a percentage change from the uptake with only 10 µM GABA and no 3 alpha-hydroxy-5alpha-pregnan-20-one in this case given the measure 100%. It is noteworthy that with the dosages of 3alpha-hydroxy-5alpha-pregnan-20-one given, the mean increase in chloride uptake is 167.7% while the change in the presence of the antagonists are not significantly different from the value 100%. This shows that the 3beta-hydroxy-5alpha/beta-pregnan or 3beta-sulfate-5alpha/delta5-pregnan/pregnen-steroids have efficiently blocked the effect of 3alpha-hydroxy-5alpha-pregnan-20-one.

In all cases 3alpha-hydroxy-5alpha-pregnan-20-one is given in increasing dosages 1=0, 2=50, 3=100, 4=150, 5=200, 6=1000, 7=3000 nM+10 µM GABA+30 µM of interacting Steroid. H=high, S=significant, NS=non significant. Statistical testing made with repeated measures ANOVA followed post hoc with lest significant difference test.

The results (FIG. 3) indicate, that this negative effect is removed or alleviated through the administration of a compound according to the present invention. The experiments were conducted using 3alpha-hydroxy-pregnan-20-one as learning disturbing substance (CAS no. 516-54-1, Table 1) and 3beta,20beta-dihydroxy-5alpha-pregnane, UC1011, (CAS 516-53-9, Table 2 and 3) as blocking substance. Rats (n=46) where injected (i.v) daily with 3beta,20beta-dihydroxy-5alpha-pregnane, UC1011 20 mg/kg (n=14), 3alpha-hydroxy-5alpha-pregnan-20-one 2 mg/kg (n=14), 3alpha-hydroxy-5alpha-pregnan-20-one+3beta,20beta-dihydroxy-5alpha-pregnane, UC1011 2:20 mg/kg (n=14), or vehicle (n=4) Animals were given four swim trials daily with maximal swimming time 120 second for each trial. The rats started to swim 8 minute after the 3alpha-hydroxy-5alpha-pregnan-20-one injection for 6 days. The performance of rats was monitored with a video camera and data was analyzed with analysis of variance (ANOVA) followed by post hoc test.

As shown earlier, the compound 3alpha-hydroxy-5alpha-pregnan-20-one inhibits spatial learning. The latency to find the platform was after 6 days with practice still in the 3alpha-hydroxy-5alpha-pregnan-20-one group above 80 seconds. The rats injected with the mixture of 3beta,20beta-dihydroxy-5alpha-pregnane, UC1011±3alpha-hydroxy-5alpha-pregnan-20-one had a lower latency time (p<0.05 day 4-6) compared with the 3alpha-hydroxy-5alpha-pregnan-20-one group showing that the rats in this group where able to learn. The group that only received 3beta,20beta-dihydroxy-5alpha-pregnane, UC1011 learned to find the platform as quickly as the control group (vehicle) and faster than the 3alpha-hydroxy-5alpha-pregnan-20-one treated rats (p<0.05 day 3-6). There was no significant difference in speed between four groups (FIG. 3).

TABLE 3

Blocking effects of tested steroids on 3alpha-hydroxy-5alpha-pregnan-20-one, measured as change in chloride uptake through the GABA-A receptor

| Steroid | Mean % (SEM) chloride uptake relative to only 10 uM GABA | Significantly different from 3alpha-hydroxy-5alpha-pregnan-20-one | Within group change from 0 nM 3alpha-hydroxy-5alpha-pregnan-20-one |
|---|---|---|---|
| Reference steroid with agonistic effect: 3alpha-hydroxy-5alpha-pregnan-20-one | 167.7(13) | — | Dose 3, 5, 6, 7 = S |
| 1) 3beta,20beta-dihydroxy-5alpha-pregnane, CAS 516-53-0, product name UC1011 | 81.9(19) | 0.001 | All dosages = NS |
| 2) 3beta,20alpha-dihydroxy-5Beta-pregnane, CAS 80-90-0, product name UC1013 | 84.2(22) | 0.003 | All dosages = NS |
| 3) 3beta-hydroxy-delta5-Pregnen-20-one, sulfate, sodium salt, CAS 1852-38-6 UC1018 | 64.7(23) | 0.001 | All dosages = NS |
| 4) 3beta-hydroxy-5beta-pregnan-20-one CAS 128-21-2, product name UC1014 | 92.9(22) | 0.012 | All dosages NS |
| 5) 3beta,21-dihydroxy-5Beta-pregnan-20-one, product name UC1015 | 102.7(22) | 0.017 | All dosages = NS |
| 6) 3beta-hydroxy-5alpha-pregnan-20-one, sulfate, sodium salt, product name UC1016 | 109.8(19) | 0.018 | All dosages = NS |
| 7) 3beta hydroxy-5alpha-pregnan-11,20-dione, product name UC1017 | 116.9(19) | 0.036 | All dosages = NS |
| 8) 3beta-hydroxy-5alpha-pregnan-20-one, CAS 516-55-2, product name UC1010 | 104.4(13) | 0.002 | Dos 7 = S H<br>The rest = NS |
| 9) 3beta-hydroxy-5alpha-pregnan-20-one-acetate, $C_{23}H_{36}O_3$, CAS number 906-83-2, product name UC1012 | 110.9(16) | 0.014 | Dos 7 = S H,<br>The rest = NS |

In Vivo Animal Studies

Animal studies using the Morris water-maze model have been performed. In the Morris water-maze model, the learning capacity of the test animals can be observed. The test animal, usually a rat, is placed in a container with water, having a platform at one location. This platform is slightly under the surface of the water, and the rat must swim until it finds the platform. In following test sessions the rat will learn were the platform is by looking at markings on the wall of the room. It is known, that the learning process is negatively influenced by the administration of CNS depressing 3alpha-hydroxy-pregnan-steroids. (Johansson L M, Birzniece V, Lindblad C., Olsson T. and Bäckström T (2002) *Allopregnanolone inhibits learning in the Morris water maze. Brain Res* 934, 125-131).

Although the invention has been described with regard to its preferred embodiments, which constitute the best mode presently known to the inventors, it should be understood that various changes and modifications as would be obvious to one having the ordinary skill in this art may be made without departing from the scope of the intention which is set forth in the claims appended hereto.

We claim:

1. A method for the treatment or alleviation of 3alpha-hydroxy-5alpha/beta-steroid induced central nervous system ("CNS") disorders in human patients, wherein 3beta,20beta-dihydroxy-5alpha-pregnane is administered to said human patient.

2. The method of claim 1, wherein said 3beta,20beta-dihydroxy-5alpha-pregnane is administered in the form of a pharmaceutical composition further comprising at least one carrier.

3. The method of claim 1, wherein said 3beta,20beta-dihydroxy-5alpha-pregnane is in the form of a sodium salt.

4. The method of claim 1, wherein said 3beta,20beta-dihydroxy-5alpha-pregnane is administered to said human patient intravenously, nasally, per rectum, intravaginally, percutaneously or orally.

5. The method of claim 4, wherein said 3beta,20beta-dihydroxy-5alpha-pregnane is administered to said human patient intravenously.

6. The method of claim 4, wherein said 3beta,20beta-dihydroxy-5alpha-pregnane is administered nasally.

7. The method of claim 1, wherein said 3beta,20beta-dihydroxy-5alpha-pregnane is administered to said human patient intravenously in doses in the interval of about 0.2 to about 200 mg per kg body weight.

8. The method of claim 1, wherein said 3beta,20beta-dihydroxy-5alpha-pregnane is administered intravenously in doses in the interval of about 20 to about 100 mg per kg body weight.

9. The method of claim 1, wherein said steroid-induced CNS-disorder is a steroid related mood disorder.

10. The method of claim 1, wherein said steroid-induced CNS-disorder is a side effect of postmenopausal hormone therapy in human patients.

11. The method of claim 1, wherein said steroid-induced CNS-disorder is a side effect of oral contraceptives in human patients.

12. The method of claim 1, wherein said steroid-induced CNS-disorder is steroid-related tiredness in human patients.

13. The method of claim 1, wherein said steroid-induced CNS-disorder is a steroid-related memory disturbance in human patients.

14. The method of claim 1, wherein said 3alpha-hydroxy-5alpha/beta-steroid induced disorder is selected from the group consisting of: epilepsy, migraine, depression, eating disorders, cognitive disorders, movement disorders, sleeping disorders, stress related disorders, menstrual cycle linked disorders, premenstrual syndrome, premenstrual dysphoric disorder; substance dependence, menstrual cycle linked epilepsy, and combinations thereof.

15. The method of claim 14, wherein said 3alpha-hydroxy-5alpha/beta-steroid induced disorder is a menstrual cycle linked disorder selected from the group consisting of: sedation, tiredness, memory disturbance, learning disturbance, concentration difficulties, disturbance of motor function, clumsiness, increased appetite and food cravings, negative mood from tension, irritability and depression, premenstrual syndrome, premenstrual worsening of Petit Mal epilepsy, stress sensitivity, loss of impulse control and depression and combinations thereof.

16. The method of claim 14, wherein said 3alpha-hydroxy-5alpha/beta-steroid induced disorder is a stress related disorder selected from the group consisting of: stress related mood changes, depression, migraine, tiredness, memory changes, sedation, memory disturbance, learning disturbance, concentration difficulties, disturbance of motor function, clumsiness, increased appetite and food cravings, negative mood from tension, irritability and depression, worsening of Petit Mal epilepsy, stress sensitivity, loss of impulse control, substance dependence, stress related epilepsy, stress related worsening of Alzheimer's dementia, post partum mood changes and combinations thereof.

17. A method for controlling and/or terminating 3alpha-hydroxy-5alpha/beta-steroid steroid anesthesia in human patients comprising administering 3beta,20beta-dihydroxy-5alpha-pregnane to a patient in need thereof.

* * * * *